United States Patent [19]

Shimazaki

[11] Patent Number: 4,528,854
[45] Date of Patent: Jul. 16, 1985

[54] PHASED-ARRAY RECEIVER

[75] Inventor: Toru Shimazaki, Tokyo, Japan

[73] Assignee: Yokogawa Medical Systems, Limited, Tokyo, Japan

[21] Appl. No.: 576,139

[22] Filed: Feb. 2, 1984

[51] Int. Cl.³ ............................................ G01N 29/00
[52] U.S. Cl. ...................................... 73/626; 128/660; 367/105
[58] Field of Search .................. 128/660, 661; 73/626, 73/625; 367/105, 122

[56] References Cited

U.S. PATENT DOCUMENTS

| | | | |
|---|---|---|---|
| 4,005,382 | 1/1977 | Beaver | 73/626 |
| 4,070,642 | 1/1978 | Iinuma et al. | 73/626 |
| 4,116,229 | 9/1978 | Pering | 73/626 |
| 4,159,462 | 6/1979 | Rocha et al. | 128/661 |
| 4,223,560 | 9/1980 | Glenn | 73/626 |
| 4,241,610 | 12/1980 | Anderson | 73/626 |
| 4,257,271 | 3/1981 | Glenn | 128/660 |
| 4,330,875 | 5/1982 | Tachita et al. | 128/660 |
| 4,372,323 | 2/1983 | Takemura et al. | 128/660 |

OTHER PUBLICATIONS

IEEE Spectrum, "Medical Diagnostics: Visual/Aural Techniques", Sep. 1977, pp. 69-70.

Primary Examiner—Kyle L. Howell
Assistant Examiner—Ruth S. Smith
Attorney, Agent, or Firm—Moonray Kojima

[57] ABSTRACT

A phased-array receiver used in an ultrasonic diagnostic apparatus or the like for appropriately varying the phases of the output voltages from transducer elements receiving ultrasonic waves and for summing these voltages to change the directional or other characteristics of ultrasonic waves. The receiver is equipped with a plurality of blocks each comprising a tapped delay line and a crosspoint switch. The crosspoint switch is capable of selecting any desired one of various delay periods of the delay line. The receiver can perform all types of scans ranging from linear scan, intermediate scan, dynamic focusing scan, to sector scan.

5 Claims, 13 Drawing Figures

PHASED-ARRAY RECEIVER

BACKGROUND OF THE INVENTION

1. Field of Invention

This invention relates to a phased-array receiver which is used in an ultrasonic diagnostic apparatus of the like, for suitably varying the phases of the voltages from transducer elements that receive ultrasonic waves, and for summing these voltages to change the directional or other characteristics or ultrasonic waves.

2. Description of the Prior Art

Electronically scanned ultrasonic diagnostic apparatuses can be classified into two categories or types according to the principles on which they operate. One type is a linear scan. Another type is a sector scan.

In a linear scan, an array of transducer elements transmits or receives ultrasonic beams directed substantially perpendicularly to the array. The transducer elements are successively excited as if one ultrasonic beam were translated for scanning purposes. Therefore, according to this type of scan, the scanning lines generated parallel to each other produce a tomogram of an object under examination.

In a sector scan, almost all of the transducer elements of an array are excited in different timed relationships, to electronically control the directions of propagation of the transmitted or received ultrasonic beams, and thereby perform a scan in the shape of a geometrical sector.

According to these different principles of operation of both types of scanning, ultrasonic diagnostic apparatuses of linear scan systems are generally used to diagnose a human abdomen, and sector scan systems are generally used to observe the interior of a human body through space between neighboring ribs, thereby to diagnose the heart or to accomplish other similar purposes.

In this manner, ultrasonic diagnostic apparatuses of linear and sector scan systems were once manufactured and operated as entirely different apparatuses.

However, in recent years, an apparatus which is functionally either a cross between the apparatuses of the mentioned two types of scans, or a device belonging to neither type, has been devised. Furthermore, ultrasonic diagnostic apparatuses have been required to perform both linear and sector scans using the same apparatus.

Figure 1:
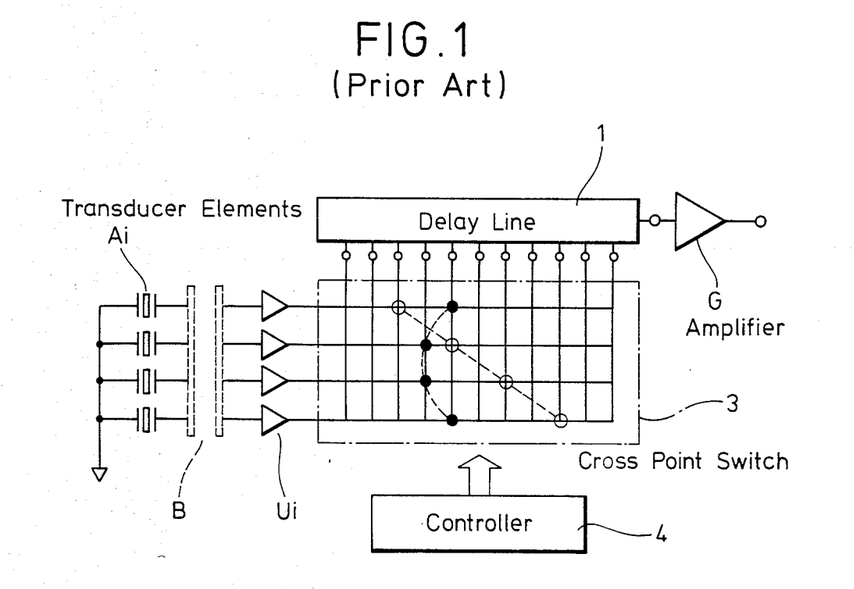
FIG. 1 is a block diagram depicting a conventional receiver used for both linear and sector scan.
Figure 3:
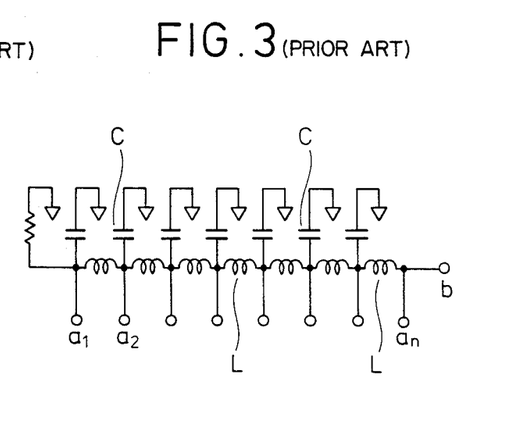
FIG. 3 depicts parts of a delay line.

An apparatus, which satisfies most of the foregoing requirements, is depicted in FIG. 1, in a general block diagram. The apparatus has a delay line 1. The delay line 1 may comprise, for example, the components depicted in FIG. 3, where each LC unit circuit comprises an inductor L and a capacitor C, provided between neighboring taps $a_1$-$a_n$, to delay input electrical signal applied thereto by equal increments of time. In this specification, a delay line means a delay line equipped with a plurality of taps, such as depicted in FIG. 3.

The system of FIG. 1 further includes a crosspoint switch 3, wherein switching elements are placed in a matrix, that is at points where longitudinal lines (output lines) and lateral lines (input lines) meet. These switching elements are opened or closed under control of a controller 4. A plurality of transducers, each of which converts electrical input signals to acoustic output signals, constitute an array $A_j$. Each transducer element is made, for example, of lead zirconate titanate (PZT). For sake of clarity, only four transducer elements are depicted in the array of FIG. 1. However, in a practical embodiment, a large number of transducer elements, for example, 32, may be provided. Also shown are a connector B and a set of amplifiers $U_j$. The outputs of amplifiers $U_j$ are connected to the lateral lines of the crosspoint switch 3. The output signal from delay line 1 is amplified by an amplifier G and supplied for use.

Although the circuit of FIG. 1 is represented as a configuration for processing signals received by array of transducer elements $A_j$, if amplifiers $U_j$ and G are bidirectional devices, the circuit can also serve to transmit ultrasonic beams from transducer elements $A_j$. Thus, circuits discussed herein can serve both transmission and reception functions. In the instant discussion, however, the components will be treated generally as receiving circuits for sake of convenience and simplicity.

If delay line 1 of FIG. 1 has a sufficiently high resolution of delay time and a sufficiently large number of taps of the delay line to accommodate both linear scan and sector scan, and if the number of switching elements in crosspoint switch 3 is sufficiently large, the receiver shown in FIG. 1, can perform both linear and sector scans. The receiver may reasonably be said to be a general purpose apparatus because all (four in FIG. 1) of the transducer elements needed to obtain a visual image can be connected to crosspoint switch 3, and because delay line 1 has a sufficiently high resolution of delay time and a sufficiently large number of taps to achieve different types of scans ranging from linear scan to sector scan. Controller 4 in such cases is used to close and open selectively any desired crosspoint in the matrix switch 3 when performing the different type of scan.

Figure 6:
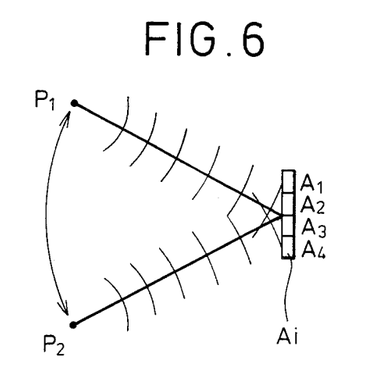
FIG. 6 depicts a sector scan.

FIG. 1 shows a configuration where the array of transducer elements $A_i$ are connected for sector scan. Thus, operation in a sector scan mode will be briefly described, with reference to FIG. 6. In FIG. 6, the manner of propagation of reflected ultrasonic waves, or echoes, is shown. As an example, an echo from point $P_1$ returns to array $A_i$ in the form of a wavefront shown in FIG. 6. Thus, the times at which the echo reaches the transducer elements differ according to the incident angle of the echo to the transducer element. Thus, in order to exactly detect the echo from point $P_1$, for example, suitable time delays are given to electrical signals which are produced from the transducer elements in response to arrival of the echo so that the electrical signals may be equivalently in phase. Since the system of FIG. 1 is equipped with an ideal delay line 1 and crosspoint switch 3, phase adjustment can be readily made as mentioned above.

Figure 2:
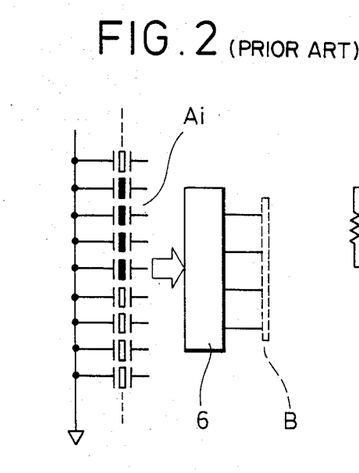
FIG. 2 depicts a structure of a probe used for linear scan.

When a linear scan is made by the system of FIG. 1, the probe for sector scan is replaced by a probe comprising an array of transducer elements $A_j$ such as depicted in FIG. 2, and connection of the latter probe is made via connector B. Generally, probes for linear scan comprise a large number of transducer elements than probes for sector scan. However, the numer of transducer elements excited for a single ultrasonic beam is equal to or less than that of sector scan. In FIG. 2, four transducer elements are excited irrespective of the type of scanning mode. These excited transducer elements are successively selected for every ultrasonic scanning beam by selector circuit 6 in the probe as shown in FIG. 2. Consequently, the receiver shown in FIG. 1 receives substantially the same number of input signals through connector B, whether the scan is made linearly or in sectorial manner. Thus, the receiver can be used for both types of scanning modes.

In linear scan, an echo enters the array of transducer elements $A_i$ at angles smaller than those in case of sector scan. Therefore, delay line 1 and crosspoint switch 3 of FIG. 1 can suitably perform linear scan. As hereinbefore described, the system of FIG. 1 can perform linear scan to sector scan, but the receiver has certain deficiencies.

For example, when a sector scan is executed by the system of FIG. 1, efficient use is made of delay line 1 and cross point switch 3. However, when the system is used for linear scan, only a small part of the delay line 1 and crosspoint switch 3 are utilized. Hence, the system of FIG. 1 is, for such purpose, redundant.

Moreover, since delay line 1 has only a single output, it is impossible to simultaneously obtain a plurality of azimuth angles or electrical echo signals emanating from a plurality of acoustic positions.

Also, only one switching element is allowed to be closed at one time for each lateral (i.e. input) line of crosspoint switch 3, as may be understood by study of the structure of delay line depicted in FIG. 3. Thus, delay line 1 operates at a low time-wise efficiency.

SUMMARY OF THE INVENTION

Accordingly, it is an object of this invention to provide a phased-array receiver which is capable of adapting itself to various kinds of scans, including linear scan, sector scan, and an intermediate between the two scans, and which has a delay line or lines operating efficiently. The intermediate scan is described, herein for example, with reference to FIGS. 9 and 10.

The phased array receiver according to the invention is used for an ultrasonic diagnostic apparatus and comprises active transducer elements, crosspoint switches, and a plurality of relatively small sized blocks (as described herein). The blocks have input lines common to them so that the signals which are produced by the transducer elements upon reception of ultrasonic waves may be applied to the blocks through the common input lines. The signals passing through the blocks are delayed and summed up in an suitable combination by action of the cross point switches. The blocks can be connected in series circuit to produce longer delay time periods for sector scan. The blocks can also be connected in parallel circuit to utilize the output signals from the blocks independently, thereby permitting high resolution linear scan. The series and parallel connections are further explained hereinbelow. The term "phased array receiver" has become known in the art to include all types of ultrasonic receivers and transmitters, and is used herein in such non-limiting manner.

DESCRIPTION OF PREFERRED EMBODIMENTS

Figure 4:
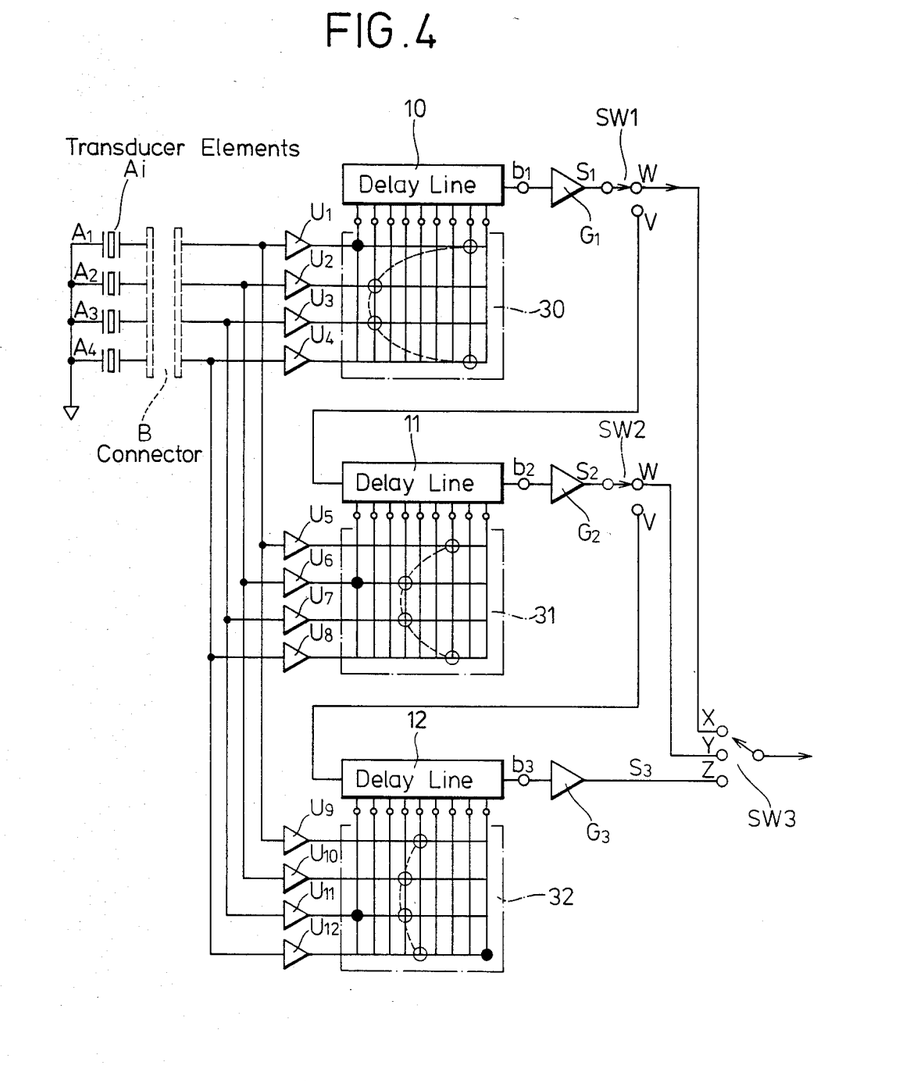
FIG. 4 and FIG. 8 are block diagrams of illustrative embodiments of the invention.

In FIG. 4, there is depicted a phased-array receiver, according to the invention, comprising delay lines 10,11,12, which are substantially identical in structure to the delay lines described in connection with FIGS. 1 and 3, except for the number of taps. Control circuits and other circuits and devices, such as used in FIG. 1, are omitted for sake of clarity of description and simplicity. Delay line 1 shown in FIG. 1 requires a relatively large number of taps, whereas each of the delay lines 10,11 and 12 in FIG. 4 needs taps whose number is approximately equal to the number of taps in delay line 1 of FIG. 1 divided by a small integer. Accordingly, each of delay lines 10,11 and 12, requires fewer number of taps than delay line 1 in FIG. 1. It is noted that delay lines 10,11 and 12 are not necessarily all required to have the same number of taps nor the same time delay per tap. The receiver further comprises crosspoint switches 30,31 and 32, connected to delay lines 10,11 and 12, respectively, as depicted. These crosspoint switches 30,31, 32 function similarly to crosspoint switch 3 described in FIG. 1. The switching elements, which like the switching elements in FIG. 1, are disposed in a matrix at points where the lateral and longitudinal lines meet, are closed or opened by a controller, which is omitted in FIG. 4 for sake of clarity of description and simplicity. Also, the drawing is representational and is not to any exact scale.

In one feature of the invention, the receiver is equipped with a plurality of blocks each comprising a delay line, a plurality of amplifiers and a crosspoint switch, as described herein. This configuration offers many advantages as herein described. Although in the illustrative embodiment in FIG. 4 three such blocks are provided, the number of blocks is not limited to three.

The novel receiver also comprises an array of transducer elements $A_1$ similar to the array described in FIG. 1. A connector B allows a linear scanning probe or a sector scanning probe to be interchangeably connected into the circuitry of the receiver. In the illustrative embodiment of FIG. 4, amplifiers $U_1$-$U_{12}$ are so constructed that a group of four make up one set. Since the number of transducer elements $A_1$ shown in FIG. 4 is four, in the same manner as in FIG. 1, the same number, i.e. four, of amplifiers are connected to each block to process four channel signals which are supplied from the array of transducer elements $A_1$ via connnector B. These four channel signals are coupled in parallel to the three sets of amplifiers $U_1$-$U_4$, $U_5$-$U_8$, and $U_9$-$U_{12}$ as depicted. Then, the signals are furnished to the respective crosspoint switches of the blocks. The circuit which receives the signals from the array of transducer elements $A_1$ and applies them to the crosspoint switches in parallel relation, is referred to herein as the input circuit.

Delay lines 10,11 and 12 have their respective output terminals $b_1$, $b_2$ and $b_3$ which are respectively connected to amplifiers $G_1$, $G_2$ and $G_3$. Switches SW1 and SW2 each have two contact points V and W. Switch SW3 has three contact points X,Y and Z. The output from amplifier $G_1$ is supplied to contact point X of switch SW3 through contact point W of switch SW1 and also to the leftmost terminal of delay line 11 through contact point V of SW1. The output from amplifier $G_2$ is provided to contact point Y of switch SW3 through contact point W of switch SW2, and to the leftmost terminal of delay line 12 through contact point V of switch SW2. The output from amplifier $G_3$ is given to contact point Z of switch SW3.

The operation of the embodiment described in FIG. 4 will now be described. It is assumed that a probe for sector scan is connected into receiver of FIG. 1. Sector scan is a scan made literally in a sectorial manner, and its principles have already been described with reference to FIG. 6. Thus, the manner in which a sector scan is made by the apparatus of FIG. 4 is used in the following description. Contact points of switches SW1 and SW2 are connected to their V sides, while switch SW3 is connected to contact point Z. An echo coming from point $P_1$ (see FIG. 6) reaches transducer element $A_1$ earliest and arrives at the transducer $A_4$ latest. Thus, in order to put the echo arriving at array $A_i$ in phase, the receiver of FIG. 4 is operated in the following manner.

The electrical signal from the transducer element $A_1$ is passed through amplifier $U_1$. Then, the signal is fed to delay line 10 via a switching element indicated by a small black circle in crosspoint switch 30. This signal is then passed through amplifier $G_1$, contact point V of switch SW1, delay line 11, amplifier $G_2$, contact point V of switch SW2, delay line 12 and amplifier $G_3$, in that order, and finally reaches contact point Z of switch SW3.

The electrical signal from transducer element $A_2$ is passed through amplifier $U_6$. Then, the signal is introduced to delay line 11 via a switching element indicated by a small black circle in crosspoint switch 31. Then, this signal reaches contact point Z of switch SW3 through delay lines 11 and 12.

The electrical signal from transducer element $A_3$ passes through amplifier $U_{11}$. Then the signal is applied to delay line 12 through switching element indicated by a small black circle in crosspoint switch 32. The electrical signal from transducer element $A_4$ arrives at contact point Z of switch SW3 after passing through amplifier $U_{12}$, switching element indicated by a small black circle in crosspoint switch 32, and delay line 12.

In the final route, no time delay occurs, because the closest element is the tap in the final stage.

Figure 5:
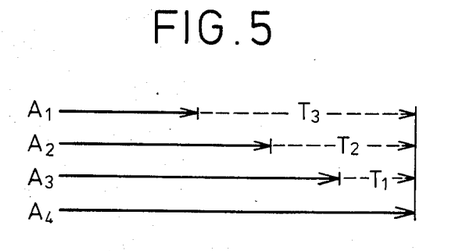
FIG. 5 depicts time delays introduced by the cooperation of a crosspoint switch and a delay line.

These operations give time delays, such as depicted in FIG. 5, to the electrical signals from transducer elements $A_1$-$A_4$, so that the output signals taken from contact point Z of switch SW3 are in phase. These time delays given to the signals are indicated by $T_1$, $T_2$, and $T_3$, in FIG. 5.

Any sector scan, as shown in FIG. 6, can be effected as desired by suitably switching, such as by use of a control circuit not shown, the elements in the crosspoint switches 30,31,32 in this manner.

When a probe for linear scan is connected into the receiver shown in FIG. 4, the receiver operates as follows. The structure of such a probe has been already described in connection with FIGS. 1 and 2 and so it will not be described hereat in detail. A general linear scan can be regarded as a sector scan having relatively small scanning angles. That is, echoes enter the transducer elements in substantially perpendicular relation thereto. Accordingly, the receiver shown in FIG. 4 can readily perform linear scan, without any substantial change in components.

Figure 7:
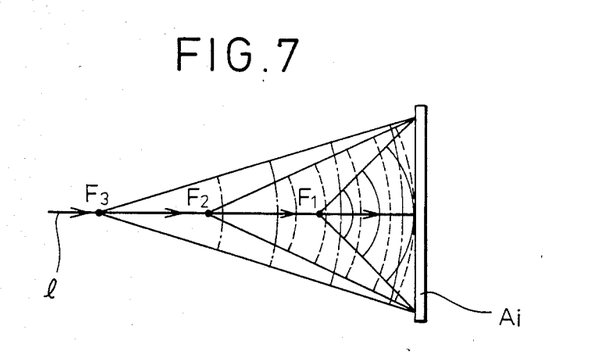
FIG. 7 depicts a dynamic focusing operation.

An example of operation in dynamic focusing mode for obtaining a plurality of foci using a single scanning line, unlike a simple linear scan, is next described by referring to FIG. 7. In FIG. 7, echoes from points $F_1$-$F_3$, which lie at different depths along a scanning beam 1, reach the array of transducer elements $A_i$ while carried by the wavefront shown. The echoes reaching the transducer elements are slightly out of phase with one another. Furthermore, these phase relationships vary among different depths of reflecting points, such as $F_1$, $F_2$ and $F_3$. Therefore, a receiver having a plurality of foci is necessary to distinctly locate the reflecting source on the scanning beam 1. The ultrasonic beam emitted by the array of transducer elements $A_i$ is first reflected as an echo from the nearest point $F_1$. Then, the beam is successively reflected as echoes from points $F_2$ and $F_3$. As such, the phase arrangement in the receiver is required to be exchanged for others according to the distances to points $F_1$, $F_2$ and $F_3$, or to the periods of time taken by the echoes to return.

A dynamic focusing scan in which the focused depth is successively exchanged for others in this way is performed by the apparatus of FIG. 4, in the manner described below. In this case, switches SW1 and SW2 are connected to contact points W. When the elements of crosspoints switches 30,31,32, indicated by small white circles in FIG. 4, are closed, a signal $S_1$ is obtained from the block comprising delay line 10 and crosspoint switch 30, under the condition that the focus is taken at the closest point $F_1$ producing a large phase difference.

Similarly, a signal $S_2$ is obtained from the block comprising delay line 11 and crosspoint switch 31, in such a state that the focus is taken at point $F_2$ in FIG. 7. Finally, in a similar manner, a signal $S_3$ is delivered from the block comprising a delay line 12 and crosspoint switch 32, under the condition that the focus is taken at point $F_3$ in FIG. 7. Thus, it is possible to obtain a composite electrical signal containing the three foci from switch SW3 by successively shifting the closed contact point from X to Y to Z. The number of foci is not limited to the aforementioned three, but can be greater or less.

Figure 8:
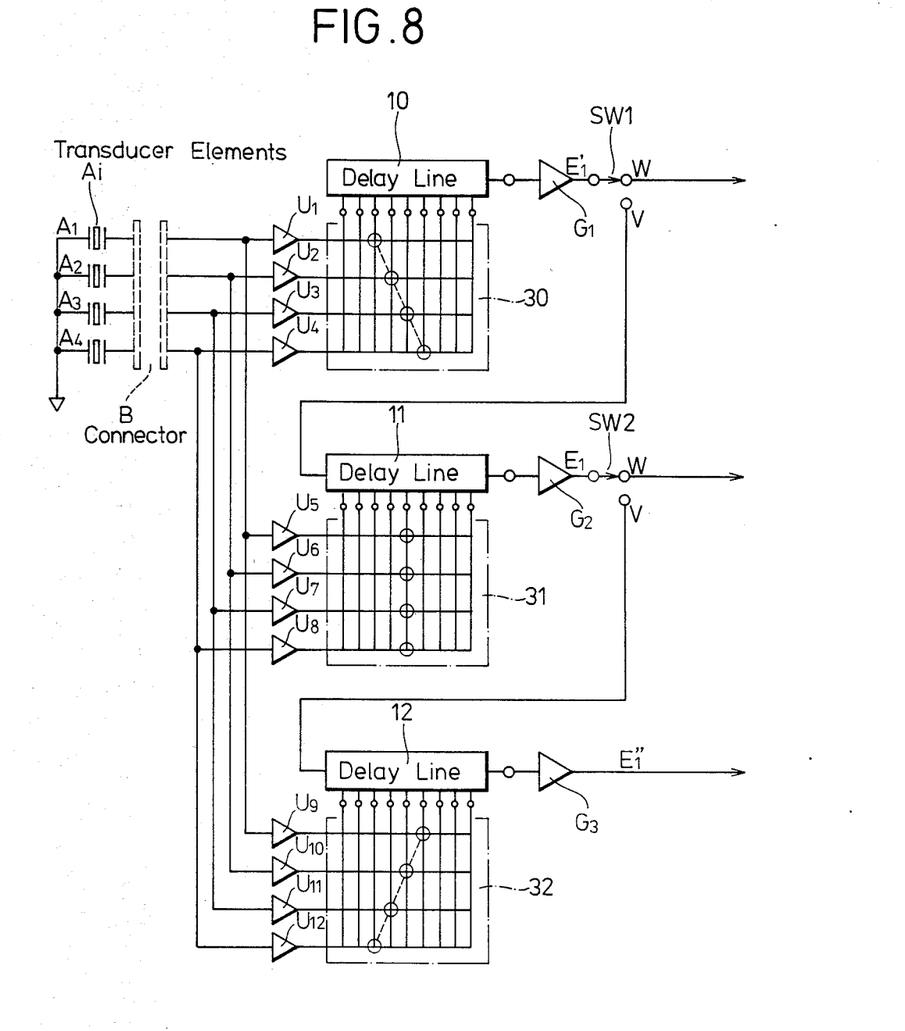

Referring next to FIG. 8, there is depicted another illustrative embodiment of the invention. This receiver is adapted for intermediate scan and is similar to the receiver shown in FIG. 4, except that switch SW3 is omitted. The components which are the same as those in FIG. 4 are denoted by the same reference numberals and will not be described hereat for sake of simplicity of description.

Figure 9:
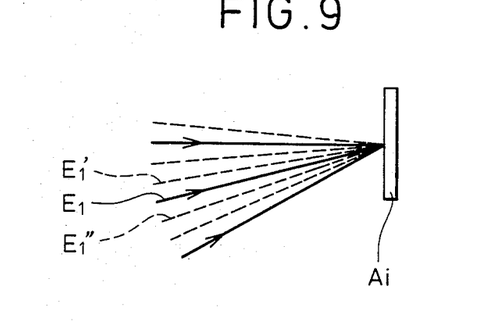
FIG. 9 and FIG. 10 depicts intermediate scans.
Figure 10:
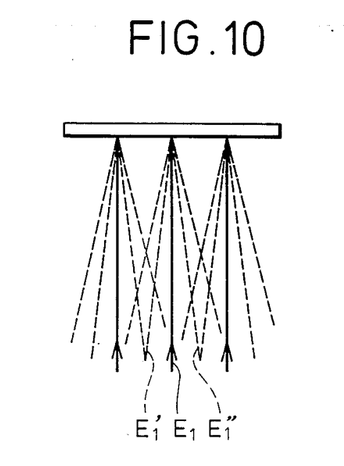

The operation for intermediate scan is now described by referring to FIGS. 9 and 10. The quality of a tomogram obtained by an ultrasonic diagnostic apparatus can be effectively enhanced by increasing the number of scanning beams. However, there is a certain limit to such an increase of number of beams, because of the need to obtain tomograms on a real time basis, and on account of the frame rate of a cathode ray display tube, the velocity of acoustic waves, and other factors. Accordingly, intermediate scan has been devised. FIG. 9 depicts an intermediate scan similar to a sector scan, FIG. 10 depicts an intermediate scan resembling a linear scan. In both FIGS. 9 and 10, the main acoustic beam $E_1$ is indicated by a solid line, while intermediate acoustic beams $E_1'$ and $E_1''$ are indicated by broken lines. These intermediate beams are obtained by slightly shifting the reception directivity to the right or left side of main beam $E_1$. As a result, the ultrasonic beam actually radiated from the array of transducer elements $A_i$ has a certain width spread about the direction indicated by the solid line. The intermediate acoustic beams indicated by the broken lines are included in the received echoes and hence the amount of image information increases. Thus, as a result, the image quality produced by the apparatus is improved.

Referring back to FIG. 8, by closing contact points W of the switches SW1 and SW2 and closing the elements of crosspoint switches 30,31,32, indicated by small white circles, the block comprising delay line 10 and crosspoint switch 30, produces a signal corresponding to the intermediate beam $E_1'$. Similarly, the block comprising delay line 11 and crosspoint switch 31, provides a signal corresponding to main acoustic beam $E_1$. Also, similarly, the block comprising delay line 12 and crosspoint switch 32 delivers a signal corresponding to intermediate acoustic beam $E_1''$. The output signals from the blocks are then separately processed to form a visual image, whereby the intermediate scanning images shown in FIGS. 9 and 10 are visualized. The operation performed when contact points V of the switches SW1 and SW2 are closed has been already described in connection with FIG. 4. Hence, such operation will not be again described.

Figure 11:
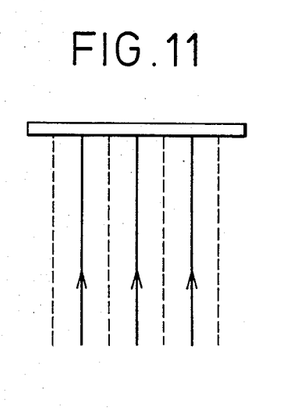
FIG. 11 and FIG. 12 depict other types of scans.
Figure 12:
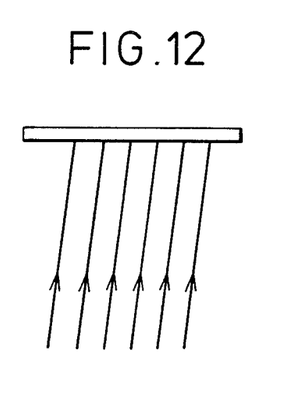

In addition to the foregoing scan, the novel receiver is capable of performing an intermediate scan such as shown in FIG. 11 and an oblique scan such as shown in FIG. 12.

Figure 13:
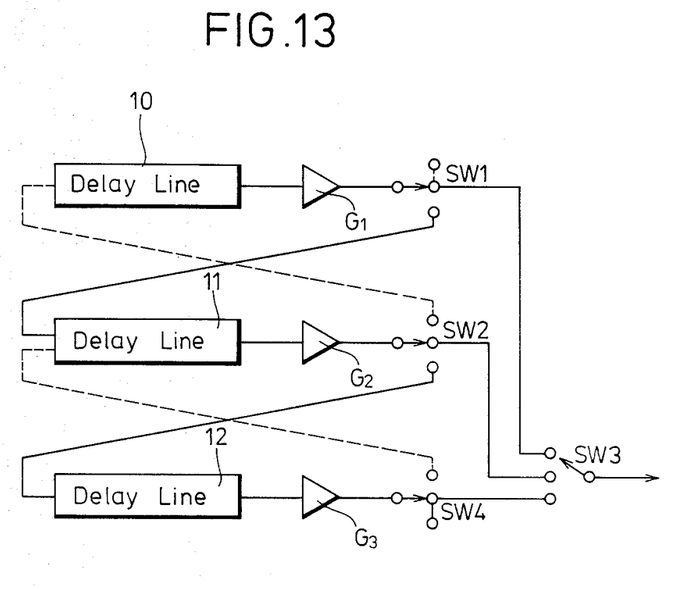
FIG. 13 depicts another connection circuit for delaying summation.

Referring next to FIG. 13, there is depicted another connecting circuitry for delaying summation, wherein the transducer elements, input circuit, crosspoint switches, etc, are omitted. The solid lines in FIG. 13 indicating routes are also used in the configuration shown in FIG. 4 and FIG. 8. In addition to these routes it is possible to introduce circuit connections indicated by broken routes in FIG. 13, in which case, the direction of scan can be reversed.

As hereinbefore described, according to the present invention, one receiver can effect every operation, ranging from linear scan to sector scan. Furthermore, since the delay lines and the crosspoint switches are used in the form of a block, the components are effectively used. In addition, a plurality of echoes of various types can be detected at one time, thus yielding great advantages. Moreover, advantageously, the receiver can be built up or reduced by suitable connection of a plurality of blocks, which blocks comprise a delay line, amplifier, and crosspoint switch. These blocks can then be connected with the delay lines connected serially in circuit, or parallel in circuit.

The foregoing description is illustrative of the principles of the invention. Numerous extensions and modifications thereof would be apparent to the worker skilled in the art. All such extensions and modifications are to be considered to be within the spirit and scope of the invention.

What is claimed is:

1. An ultrasonic receiver for receiving and transmitting ultrasonic waves using an array of transducer elements; converting received ultrasonic waves into electrical signals and delaying the phases of said electrical signals and processing the signals; said receiver comprising:
   a plurality of blocks, each of said blocks comprising a delay line having a plurality of taps, a plurality of amplifiers for receiving input signals from said array of transducer elements, and a crosspoint switch comprising a plurality of longitudinal lines, a plurality of lateral lines, and a plurality of switching elements arranged in a matrix at the intersections of said lateral and longitudinal lines, said longitudinal lines being connected to said plurality of taps of said delay line, and said plurality of lateral lines being connected to said plurality of amplifiers;
   means for commonly connecting each element of said array of transducer elements to respective ones of said amplifiers of each block; and
   switching means for selectively switching output signals from said delay lines of each of said blocks to be in parallel circuit or in series circuit to each other.

2. The receiver of claim 1, further comprising means for selectively operating said switching elements of said blocks to cause their respective output signals to be put in phase in conformity with their respective positions of echo sources lying at different depths.

3. The receiver of claim 2 wherein said switching means includes means for causing said output signals to be successively taken from said blocks.

4. The receiver of claim 1, further comprising means for selectively operating said switching elements to cause respective ones of said blocks to generate signals having different directional characteristics.

5. The receiver of claim 2, wherein said switching means and said means for selectively operating further includes means for causing the output signals from said blocks to be dynamically switched with predetermined order of time relationship.

* * * * *